United States Patent [19]

Rubey

[11] Patent Number: 4,923,486
[45] Date of Patent: May 8, 1990

[54] GAS CHROMATOGRAPHY METHODS AND APPARATUS

[75] Inventor: Wayne A. Rubey, Vandalia, Ohio
[73] Assignee: University of Dayton, Dayton, Ohio
[21] Appl. No.: 288,517
[22] Filed: Dec. 22, 1988
[51] Int. Cl.$^5$ .............................................. B01D 15/08
[52] U.S. Cl. .................................... 55/67; 55/197; 55/208; 55/270; 55/386
[58] Field of Search ............... 55/67, 197, 386, 208, 55/270, 274; 73/23.1

[56] References Cited

U.S. PATENT DOCUMENTS

| | | | |
|---|---|---|---|
| 3,043,127 | 7/1962 | De Ford et al. | 73/23 |
| 3,043,128 | 7/1962 | Ayers | 73/23.1 |
| 3,057,183 | 10/1962 | De Ford | 55/67 X |
| 3,146,616 | 9/1964 | Loyd | 73/23.1 |
| 3,149,941 | 9/1964 | Barnitz et al. | 73/23.1 X |
| 3,225,521 | 12/1965 | Burow | 55/67 |
| 3,438,243 | 4/1969 | Parks, Jr. et al. | 73/23.1 |
| 3,449,938 | 6/1969 | Giddings | 55/67 X |
| 3,486,299 | 12/1969 | Weiser, Jr. et al. | 55/67 |
| 3,538,744 | 11/1970 | Karasek | 73/23.1 |
| 3,581,465 | 6/1971 | Haruki et al. | 55/67 |
| 3,949,806 | 4/1976 | Dunges | 55/67 X |
| 4,042,350 | 8/1977 | Phillips | 55/67 X |
| 4,067,227 | 1/1978 | Johns et al. | 73/23.1 |
| 4,181,508 | 1/1980 | Schmid et al. | 55/82 |
| 4,293,415 | 10/1981 | Bente III et al. | 210/198.2 |
| 4,376,641 | 3/1983 | Nestrick et al. | 55/67 |
| 4,484,061 | 11/1984 | Zelinka et al. | 73/23.1 X |
| 4,726,822 | 2/1988 | Cates et al. | 55/386 X |

FOREIGN PATENT DOCUMENTS 897267 5/1962 United Kingdom .................... 55/67

OTHER PUBLICATIONS

Nogare et al., "Programmed Temperature Gas Chromatography", Analytical Chemistry, vol. 32, No. 7, Jun. 1960, pp. 767-770.
"Multidimensional High Resolution Gas Chromatographic Investigations of Hydrocarbon Fuels and Various Turbine Engine Fuel Precursors", Wayne A. Rubey.
"New Variant of Chromathermography", Institute of Petrochemical Synthesis, Academy of Sciences of the USSR, Zavodskaya Laboratoriya, vol. 36, No. 11, pp. 1299-1301, Nov. 1970, Berezkin et al.
"Temperature Gradients in Gas Chromatography", Journal of Chromatography, 373, pp. 21-44 (1986), Berezkin et al.
"New Method of Thermochromatographic Analysis", Zavodskaya Laboratoriya, vol. 45, No. 12, pp. 1082-1084, Dec. 1979, Zizin et al.
"Chromathermodistillation and Overloaded Chromathermography", Yanovskii et al, Russian Journal of Physical Chemistry, 55(7), pp. 1024-1026 (1981).
"Application of Chromatography for the Determination of Impurities", Berezkin et al, Chromatographia, vol. 8, No. 8, pp. 395-398, Aug. 1975.
"Chromatographie en Phase Gazeuse Realisee Simultanement avec une Programmation de Temperature et une Programmation du Gradient Longitudinal Negatif De Parametres—Theorie de la Reetention et Influence des Parametres", Coudert et al, J. Chromatogr. 58 (1971) 159-167.

Primary Examiner—Robert Spitzer
Attorney, Agent, or Firm—Biebel, French & Nauman

[57] ABSTRACT

Gas chromatographic methods and apparatus are disclosed whereby improved separation times and efficiency are achieved by provision of a time-programmable curvilinearly-shaped negative temperature gradient along the length of the chromatographic column. The gas phase sample traveling through the column always passes to a column zone having a lower temperature than the previous column zone. Accordingly, upon elution, sample bandwidths are compressed. Separation times may be decreased when compared to conventional isothermal or temperature programmed gas chromatography.

31 Claims, 6 Drawing Sheets

GAS CHROMATOGRAPHY METHODS AND APPARATUS

FIELD OF THE INVENTION

The present invention pertains to improved methods and apparatus for gas chromatography that are capable of rapidly imparting a time-programmable, and variable, versatile curvilinearly-shaped negative temperature gradient along the chromatographic column, specifically a temperature compliant open tubular column (OTC). This curvilinearly-shaped gradient can be envisioned as a three-dimensional surface of practically limitless variations in form. These programmed, curvilinear gradients will be referred to in the text as temperature surfaces.

BACKGROUND OF THE INVENTION

Gas chromatography (GC) was introduced in 1951 and is now the most widely used instrumental chemical analysis technique. By use of GC, various components of a volatile sample stream may be separated. The technique includes the recovery and/or detection of one or more specific chromatographic fractions from a gas effluent stream exiting from the chromatographic column. The gas effluent stream typically comprises a carrier gas and a series of separated fractions of the sample in the gas phase. These fractions are eluted or withdrawn from the column outlet in a particular order and over a particular time interval.

At present, isothermal gas chromatography (ITGC) and programmed temperature gas chromatography (PTGC) are commonly practiced. The instrumentation required to implement these two modes of operation is widely available. In both of these techniques, a separation column is centrally placed within a thermally controlled chamber, specifically a GC oven. In ITGC operation, the column temperature is maintained constant. In contrast, in PTGC operation, the whole column temperature is increased as a function of time from a low initial value to some elevated setting. In both of these two modes of gas chromatography, temperature is constant along the column axis.

Although there are no commercially available chromatographs capable of imparting a negative-temperature gradient along the column axis, these types of gradients have been provided in chromathermographic methods. Basically, chromathermography component separation is achieved by moving a temperature field along the length of the chromatographic column. Both stationary and non-stationary methods have been practiced. I define non-stationary chromathermography as one method in which a moving oven is used. This moving oven contains a linear temperature gradient along the oven axis so that the temperature at the beginning of the oven is higher than at its opposite end. The oven is moved axially along the column length so that the direction of the moving temperature field coincides with the carrier flow.

I define stationary chromathermography to mean that there is no moving oven in the method. A fluid, most often a liquid, is used to deliver the desired temperature gradient with the gradient being a negative value. In addition to a fluid, electrical heaters can be used to achieve the same objective. Most often, the temperature gradient is linear in nature.

Although a myriad of analyses are conducted annually using GC, many areas of technological improvement are still needed. For instance, there is a need in the art for the provision of an apparatus and method that reduce analysis times and can provide effective separation of heretofore difficult-to-separate samples. Additionally, there is a need for a device and method suited to analyze even trace-levels of particular sample components.

Prior Art

The provision of a negative temperature gradient along a gas chromatographic column is not new. For instance, in U.S. Pat. No. 3,043,127 (De Ford et al), a stepwise negative temperature gradient is provided along the column length, as shown in FIG. 2 of this patent. In the embodiment shown in FIG. 4, heaters 10, 11 are caused to travel along the chromatographic column via means of a rotatable platform on which they are mounted.

The patent to Loyd, U.S. Pat. No. 3,146,616, discloses use of a moving heater that is provided in conjunction with a chromatographic column. This patent is silent with respect to whether a negative gradient or a positive gradient (i.e., increasing temperature from upstream to downstream in the column) is provided.

Schmid et al U.S. Pat. No. 4,181,508 is noteworthy in that a method for separating desublimatable components from gas mixtures is described wherein the gas mixture flows through the separator from a warmer end toward a colder end thereof.

Linear negative temperature gradients are mentioned in gas chromatography methods in Appendix "B" of "Multidimensional High Resolution Gas Chromatographic Investigations of Hydrocarbon Fuels and Various Turbine Engine Fuel Precursors" by Rubey in 1985. A negative linear gradient is also discussed by Berezkin et al in "New Variant of Chromathermography", Institute of Petrochemical Synthesis, Academy of Sciences of the USSR, Zavodskaya Laboratoriya, Vol. 36, No. 11, pp. 1299-1301, Nov. 1970.

"Temperature Gradients in Gas Chromatography", *Journal of Chromatography*, 373, pp. 21-44 (1986), summarizes the state of the art in chromathermography and other techniques wherein temperature gradients are provided along the separatory column in gas chromatography methods. At pages 33-34 of the article, Zizin and Makov's contribution is described as being a "new moving gradient variant of chromathermography". In the device, a chromatographic column is enclosed in a casing. The casing of the column is connected with a pump to move a liquid coolant through the casing around the column. The column and casing are contained within an enclosure maintained at a constant temperature. The article states that the installation produces the chromathermographic effect by the pumping rate of the liquid coolant. The use of a large enclosure for the column, and the use of a liquid coolant with a packed column limit the rate at which the column temperature can be changed and therefore limit the speed of analyses, and in general, the chromatographic efficiency of the system.

In the Zizin and Makov article entitled, "New Method of Thermochromatographic Analysis", Zavodskaya Laboratoriya, Vol. 45, No. 12, pp. 1082-1084, December 1979, the method described above could be modified by simply programming the formerly thermostated oven. The limitations encountered above are further exacerbated by programming the temperature.

Other articles of interest to chromathermography or traveling temperature gradients, in general, include: "Chromathermodistillation and Overloaded Chromathermography", Yanovskii et al, *Russian Journal of Physical Chemistry*, 55(7) pp. 1024–1026 (1981); "Application of Chromatography for the Determination of Impurities", Berezkin et al, *Chromatographia*, Vol. 8, No. 8, pp. 395–398, August 1975; and "Chromatographie en Phase Gazeuse Réaliseé Simultanément avec une Programmation de Température et une Programmation du Gradient Longitudinal Négatif De Temperature—Théorie de la Réetention et Influence des Paramétres." Coudert et al, J. Chromatogr. 58 (1971) 159–167.

Despite the efforts of the prior art, there remains a need for a practical gas chromatographic method and apparatus that is capable of analyzing difficult-to-separate mixtures quickly and accurately. There is an even more specific need to provide such a method and apparatus that is capable of analyzing even trace quantities of a sample component. A practical device and method that can also provide for distinct, decreased size solute band-widths to facilitate sample component identification are highly desirable.

SUMMARY OF THE INVENTION

The present invention provides an infinite variety of non-planar curvilinearly-shaped negative thermal gradient fields along the length of a chromatographic column, a temperature compliant OTC. This variety provides an infinite number of "temperature surfaces" as shown in FIGS. 1–4. From here on, these curvilinear gradients will be referred to as temperature surfaces, to be consistent with accepted practice of the vertical axis indicating the key variable. The thermal gradient fields can be programmed as a function of time to provide three-dimensional (i.e., distance, x; temperature, y; time, z) temperature surfaces that are used to facilitate quick analysis of heretofore difficult-to-separate samples. The facilitation is a consequence of the many operating variables (as discussed under "Detailed Description of the Preferred Embodiment") available within this technique.

Due to the fact that the invention provides for reconcentration of the sample as it proceeds down the OTC, the requirements of the sample introduction step are less critical than for conventional techniques.

With the use of an axial sheath assembly it is possible to subject the entire length of the OTC to a precisely controlled curvilinearly-shaped declining temperature gradient. This is accomplished by placing the OTC concentrically within an insulated conduit of undulated geometry through which passes a time-programmed flow of pre-cooled, pre-heated, or locally heated fluids, particularly gases. In addition, this sheath design also permits time-programmable co-current or counter-current flows of cryogenic fluid, such as liquid $N_2$ or cooled $N_2$ gas, to be admitted to the OTC assembly. The sheath also contains a resistance heating element which is positioned parallel to the axis of the OTC. The sheath assemblies are designed to allow for rapid cooling and heating of the column. Furthermore, the column should be capable of responding to and accurately reflect the applied rapid temperature changes.

By applying separately, or in combination, controlled heating of the heat transfer fluid (typically $N_2$ gas and/or cryogenic $N_2$) and the electric resistance element, an enormous range of different time-dependent curvilinearly-shaped thermal gradient fields can be applied to the OTC. This dual and precise heating of the sheath interior produces a smooth temperature decline at every location along the length of the OTC as the sample to be analyzed travels from the injector-end of the column to the outlet detector end. The smooth temperature decline is a consequence of the rapid gas flow, undulated flowpath, and special design of the heat exchanger. The configuration or design of the heat exchanger includes a transpiration mechanism (e.g., a gas permeable barrier or perforated divider) for producing a controllable gas exchange into or from the column conduit. The application of such a special heat exchanger design assures that there will be no temperature inversions throughout the column length. It is through the use of this column axial sheath design, in conjunction with the fluid heating means and resistance heating means, that highly versatile, time programmable, and reproducible curvilinear gradient contours can be produced throughout the OTC. In addition, these contours can be rapidly induced. Furthermore, because of the low temperature inertia, after completion of one analysis, another can be started with minimal delay.

The configuration of the column sheath assembly can be either a concentric tubular construction or the sheathed flowpath can take the form of a special laminate assembly which is constructed of two close-fitting members. The completed column sheath assembly is then connected between the injection port and the detector of a gas chromatograph. A time programmable power supply may be operatively connected to the resistance heater means to provide a multiplicity of temperature versus time profiles to the heater during the analysis. Similarly, time and/or fluid pressure programmers may be connected to the fluid heater means to meet a variety of time, temperature and flow rate requirements for heating and/or cooling selected portions of the separatory column.

This mode of gas chromatography (GC) is intended to produce an enormous variety of curvilinear negative thermal gradient profiles which are time programmable to form three-dimensional surfaces. It is the column sheath assembly which permits this array of controlled declining thermal profiles to be generated. It is also this column sheath assembly that permits the serial connection of several of the column sheath assemblies, i.e., 2–10, for the purpose of enhancing the resolving power, or the selective resolution of compounds present in very complex mixtures. This multi-dimensional separation mode is largely responsible for the capability to perform trace and ultra-trace-level analyses.

DETAILED DESCRIPTION OF THE PREFERRED EMBODIMENT

In accordance with the invention, a curvilinearly-shaped negative temperature gradient is imposed along the length of a gas chromatographic column. The column used is a fused silica open tubular column of the type described in U.S. Pat. No. 4,293,415 (Bente III et al). As is used herein, the word "curvilinear" means continuously non-linear functionality and is devoid of abrupt transitions. Curvilinear motion is like the trajectory of an electron in a magnetic field. Instantaneous transitions, discontinuities, and step functions are not of a curvilinear nature. In contrast, ITGC and PTGC can be viewed as providing time independent and time dependent planar surfaces respectively. In accordance with the present invention, the generated temperature surface is always non-planar.

In accordance with the invention, the temperature at the inlet, upstream location of the column, is, throughout most of the desired analysis, maintained higher than the outlet, downstream column end temperature. It is only at the end of the analysis that the outlet temperature in any way approximates the inlet temperature.

As opposed to the prior art provision of a negative, linear gradient along the column or a step-wise negative gradient along the column length, the present invention provides a curvilinearly-shaped negative temperature gradient from upstream sample inlet to downstream sample elution location. Provision of such a curvilinear negative gradient is advantageous in comparison with the prior art techniques in that it provides a convenient and versatile means to optimize, with respect to time, the separation of complex mixtures. By way of contrast, when a column is operated in the isothermal mode, the only means available to optimize the separation with respect to time is through a change in the temperature of the entire column.

In programmed temperature gas chromatography, the initial and final column temperatures are varied in addition to applying a variety of programming rates to the column. The programmed rates of change typically range from 1° C./min. to 15° C./min. Additionally, the programming rate may be stopped at any given point in time, followed by subsequent resumption of programming at the same or at a different rate.

Accordingly, under both the isothermal and programmed temperature gas chromatography techniques, there are only a limited number of alternatives that can be varied in order to optimize the separation. These alternatives are initial temperature, final temperature and the rate at which the entire column temperature is programmed. In isothermal and programmed temperature gas chromatography techniques, the band-widths of the eluting or emerging zones either increase or stay reasonably constant with time.

A decrease in band-widths can be achieved by the application of a reconcentration mechanism. While a linear negative gradient or a step-wise gradient chromatography technique provides for band-width reconcentration, they do not provide for optimal reconcentration for most separation problems.

Provision of programmed temperature surfaces in accordance with the invention provides a much larger number of variables that may be used in order to time-optimize most separations. In addition to providing a convenient and effective means to optimize the separation with respect to time, the application of three-dimensional curvilinear gradients of varying contours with respect to axial distance, temperature, and time produce effective reconcentration of the chromatographic bands.

For instance, in accordance with the present invention, the following parameters may be varied in order to optimize the chromatographic separation.

| Term | Description |
|------|-------------|
| $T_b$ | Beginning temperature (at column entrance) |
| $T_f$ | Final temperature (at column exit) |
| (T vs z) | Temperature versus distance contour (along the column) |
| $V_m$ | Average velocity of the carrier gas |
| $t_h$ | Holding time (after insertion of the sample and before starting program) |
| ($T_f$ vs t) | Final temperature versus time contour |
| ($V_m$ vs t) | Carrier velocity versus time contour |
| (z,T,t) | Distance (measured along the column), temperature, time (three-dimensional contour) |

In addition, in accordance with the present invention, the sample introduction process can be optimized by changing $T_b$, $t_h$, and the gradient (T vs z).

The invention will be further described in connection with the appended drawings, wherein.

It is critical to the invention that the combination of chromatographic column and temperature control means (e.g. resistance heater means and/or fluid heater means) therefor possess a low temperature inertia so that the column rapidly responds to the heating or cooling patterns being imposed thereon. By the phrase "low temperature inertia", I mean that the column and associated heat exchange mediums must be capable of transferring changes of at least about 0.5° C. per second from the temperature control means to column location. For example, to meet a time objective of a 100-second analysis, I had to deliver a temperature change at the outlet ($T_f$ of about 5.5° C. per second. However, with my instrumentation, I have reached temperature changes approaching 30° C. per second. The column, in accordance with conventional techniques, is coated along its i.d. with a poly(methylsiloxane) SP-2100 or a poly(ethylene oxide) Carbowax 20M coating to act as a stationary phase. Other coatings such as phenylmethyl siloxane, cyanosiloxanes, liquid crystals, or chiral phases may be employed. The choice of coatings depends on the type and complexity of the sample to be analyzed. Additionally, columns employing two or more different phases may be employed in serial connection of the chromatographic column assemblies in accordance with the invention.

Turning now to the drawings, FIGS. 1–4 indicate three-dimensional cartesian coordinate (x, y, z) graphs showing temperature surfaces readily applicable to a chromatographic column. The x axis represents the various locations along the separatory column length proceeding from the upstream sample injection port of the column to the downstream elution opening. The y axis indicates the temperature and the z axis indicates time. As can be seen from these figures and with specific attention drawn to the x axis of each, the desired shape of the negative temperature gradient from upstream column location to downstream column location is a curvilinear shape with the downstream elution opening being maintained at a lower temperature than the upstream temperature. As used herein, "curvilinearly-shaped negative temperature gradient surface" signifies three dimensional (time, temperature, and column location) relationships such as those depicted in FIGS. 1-4.

Figure 1:
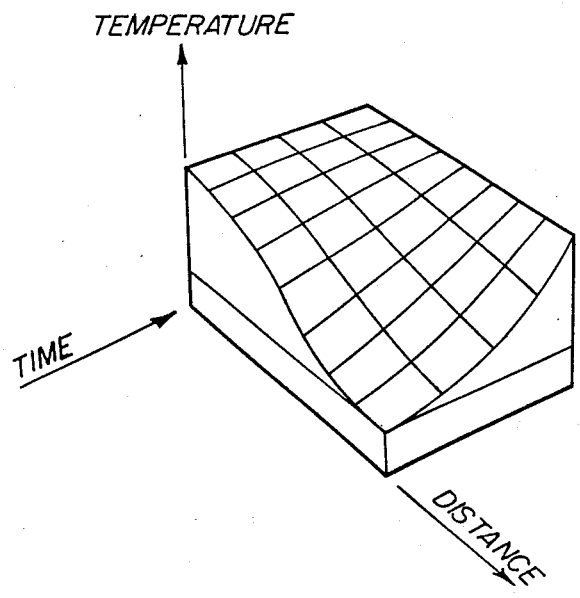
FIGS. 1–4(a–h) are three-dimensional graphs showing the relationship between axial distance, temperature, and time of gas chromatographic processes in accordance with the invention.
Figure 2:
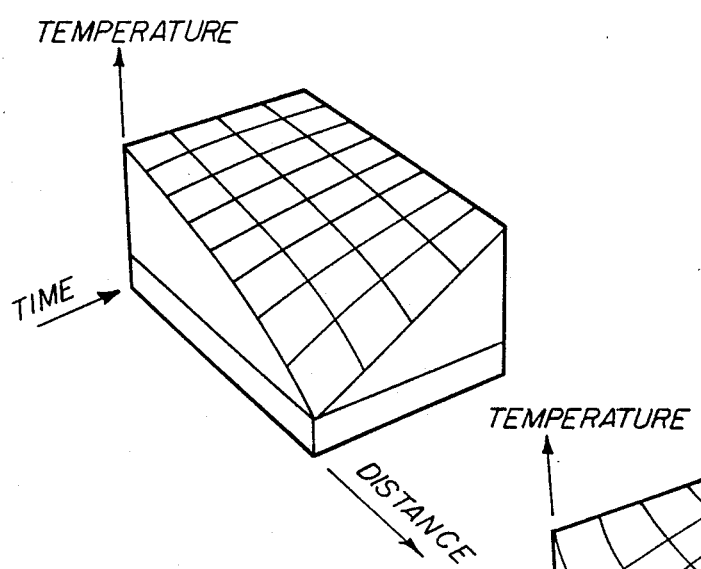
Figure 3:
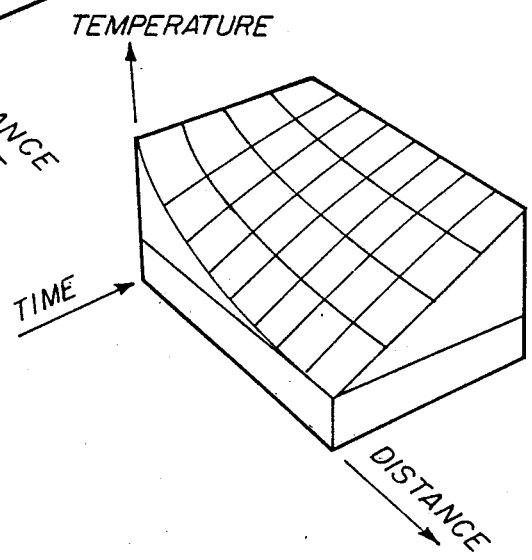
Figure 4A:
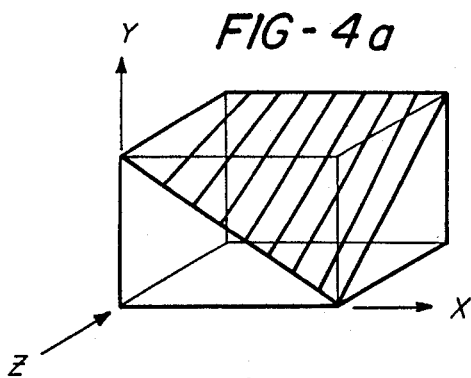
Figure 4E:
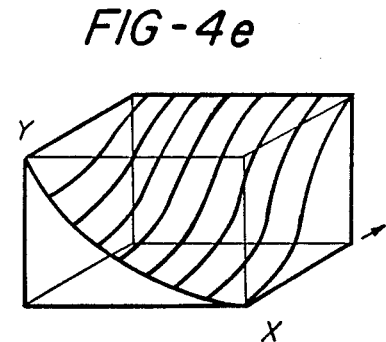
Figure 4B:
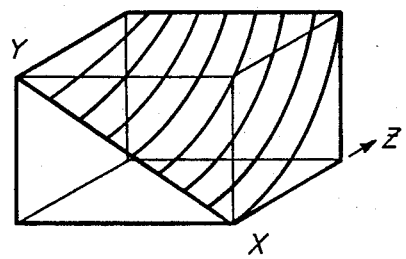
Figure 4F:
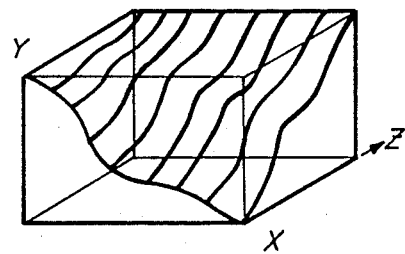
Figure 4C:
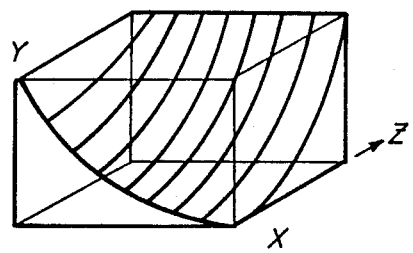
Figure 4G:
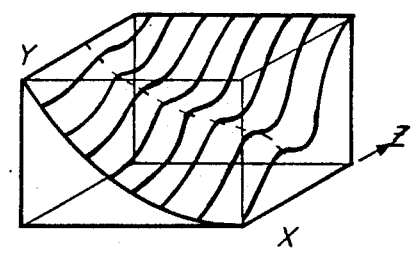
Figure 4D:
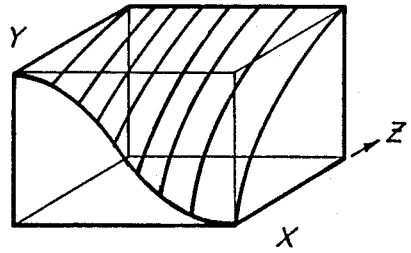
Figure 4H:
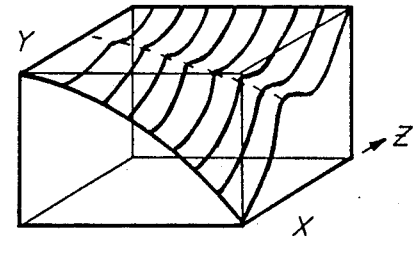

Although applicant is not to be bound to any particular theory of operation, in accordance with the invention, the gaseous sample will continually be passed to a lower temperature region as it travels down the separatory column to provide continuous refocusing of the chromatographic bands. As an analysis or separation proceeds in time, the overall column temperature is increased so that at the desired analysis end-point time, the downstream elution opening temperature reaches approximately the same temperature as the sample inlet port so that the sample will be eluted. However, at any given time, the column temperature may not be increased, as shown in FIGS. 4g and 4h. Although the temperature gradient imposed along the column (the x axis) must be negative and curvilinearly-shaped throughout almost the entire analysis, the overall temperature gradient of the column, as shown in FIGS. 4a-4h may be programmed in a wide variety of ways.

Figure 5:
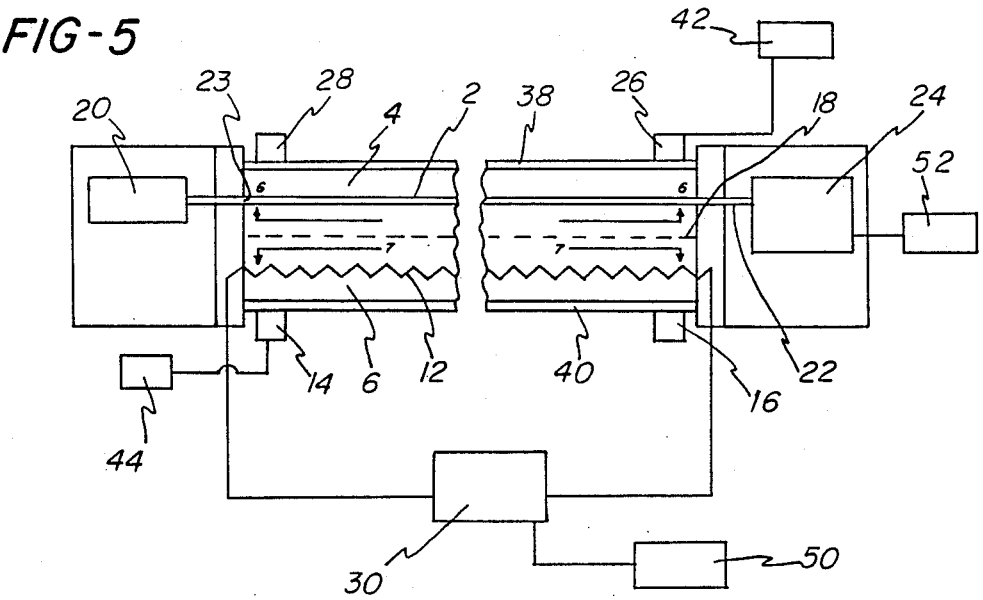
FIG. 5 is a schematic drawing of the preferred apparatus.
Figure 6:
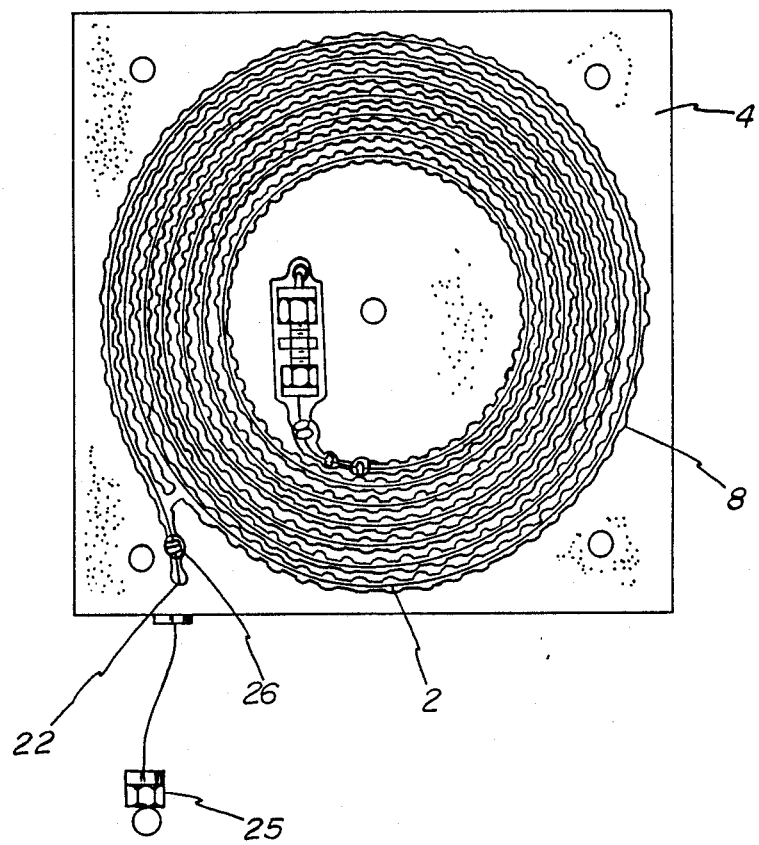
FIG. 6 is a sectional view of the apparatus depicted in FIG. 5, taken along the lines and arrows 6—6 shown in FIG. 5.
Figure 7:
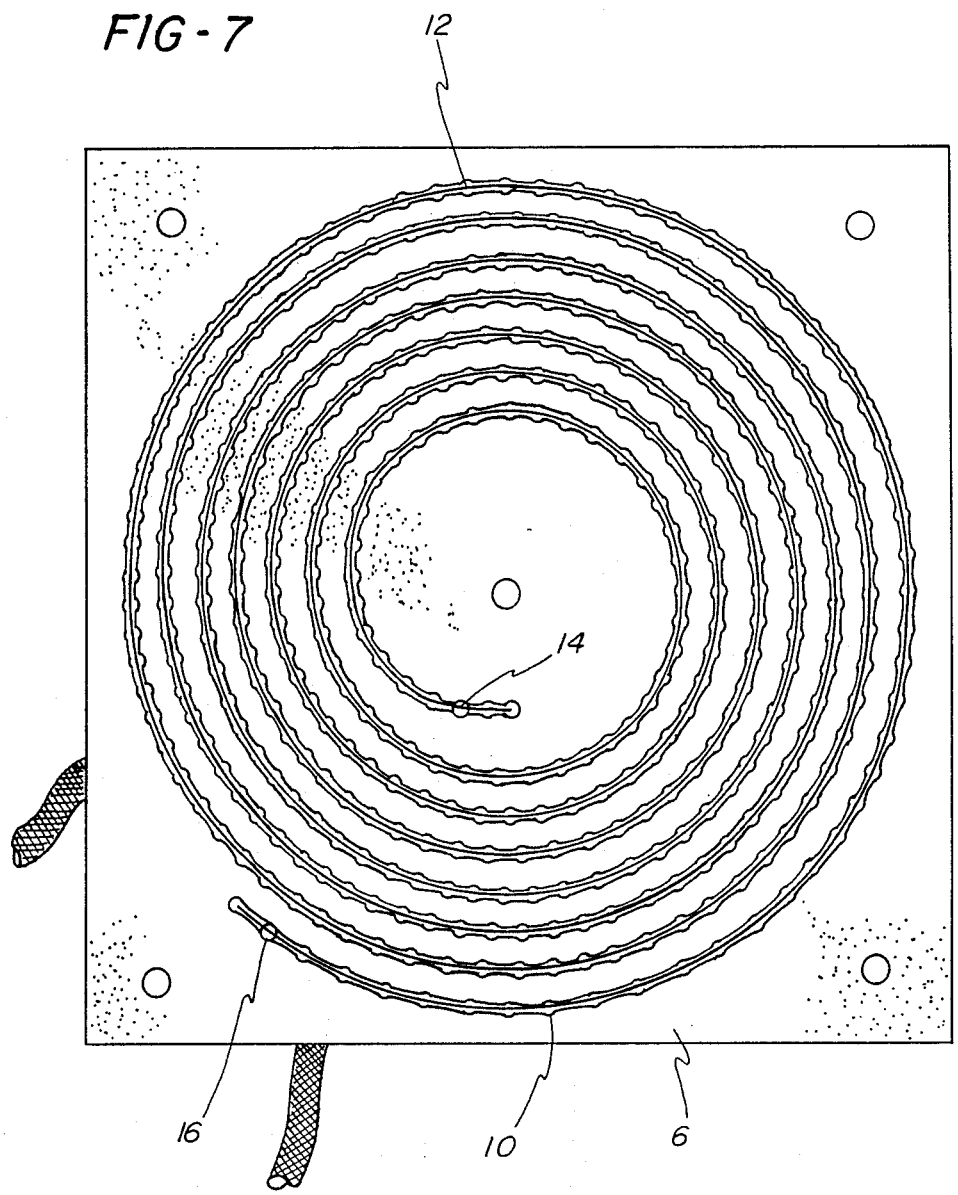
FIG. 7 is a sectional view of the apparatus depicted in FIG. 5, taken along the lines and arrows 7—7 shown in FIG. 5.

FIGS. 5-7 depict a preferred apparatus that, in accordance with the invention, provides the desired temperature surface. Open tubular column 2, preferably fused silica capillary, is interposed between top plate 4, and opposed bottom plate 6, both of which plates are preferably composed of "Marinite P" from Johns-Manville Corp. This particular material was chosen for a variety of reasons. First, it provides good electrical and thermal insulation and is capable of withstanding temperatures on the order of about 500° C. Also, it is readily machinable. Any material providing such characteristics may be utilized. For instance, it is presently thought that "Zircar 100", an impregnated ceramic fibrous material, available from Zircar Products, Inc., Florida, N.Y., may be used.

Plates 4, and 6 may be held together via conventional mechanisms such as by bolts, etc. threaded through aluminum cover plates 38, 40. As shown best in FIGS. 6 and 7, the inner portion of plates 4 and 6 is provided with generally concentric grooves 8, 10, respectively, that are provided with undulating segments for intense gas-phase mixing along the groove length. A resistance heating element 12 such as nickel chromium alloy conductor wire, is disposed within grooves 10 formed within bottom plate 6 and is operatively connected to an electrical source 30, such as a Variac so that heat may be applied throughout the grooves located on the bottom pate and thus along the OTC.

In the embodiment shown, wire 12 is a multi-stranded resistance wire covered with a braided sleeve of "Samox" insulation. "Samox" is a trademark of Briskheat Co. The wire 12 has a room temperature resistance of about 63 ohms.

The bottom plate is also provided with gas ports 14 and 16 both communicating with endwise portions of groove 10 so that a fluid, such as room temperature N$_2$ gas, can be circulated through the grooves in the bottom plate with either port 14 or 16 serving as the gas inlet and the other port providing gas exit.

Interposed between bottom plate 6 and top plate 4 is a woven piece of quartz fabric 18 which functions to allow gas exchange from the grooves in bottom plate 6 to the grooves in top plate 4. The fabric 18 allows for gas diffusion and convection forces to provide gas exchange between the grooves 8 and 10.

Grooves 8 in top plate are congruent with grooves 10 in lower plate. Together, the mating grooves 8, 10, when in superposition, form an insulating sheath that surrounds the OTC 2 and resistance heating element 12. OTC 2 is disposed in the groove 8 with the upstream sample injection port for the OTC being schematically shown as 20 and downstream elution port shown as 22. A detector 24, such as a hydrogen flame ionization detector, is disposed adjacent elution port 22 and, as is well known in the art, may be operatively connected with a recorder 52 so as to provide the chromatogram for a sample to be analyzed. A connector 25 is provided to effect connection of the OTC to the detector 24. A union 23 provides connection of the injector to the injection end of OTC 2.

Top plate 4 is provided with gas port 26 in communication with the downstream portion of grooves 8 and gas port 28 in communication with an upstream location of grooves 8. These ports provide ingress and egress of a cold fluid such as N$_2$ gas at around $-100°$ C., preferably from a downstream to upstream direction in groove 8 (using port 26 as an inlet and port 28 as an outlet) and thus from a downstream to upstream direction along OTC 2 disposed in the groove 8.

Heating filaments 12 are operatively connected with a variable voltage source 30 and optional time programmer means 50 so as to impart different temperature versus time profiles to the resistance filament 12. Thermocouples (not shown) may be disposed along OTC 2 so as to provide temperature indication of OTC 2 at the sample inlet ($T_b$), intermediate column location ($T_m$), and the elution end ($T_f$) of the column. A preferred time-temperature programmer means 50 comprises the Hewlett-Packard Model HP-3314A function generator coupled with a Model HP 6010A programmable autoranging power supply.

Additionally, as shown in FIG. 5, the flow and/or pressure of fluid flow through the ports 14, 16, and 26, 28 can be time, temperature, and pressure programmed via programmers 42, 44 which are generally designated in box form. Acceptable programmers include the Model 201 programmer from Ionics Research that operates at up to 200 psig inlet pressures, and the Model FP-2078 flow programmer available from Analabs, Inc. Although all of these devices are collectively referred to as fluid heating means, they can, of course, cooperate to actually provide cooling to the OTC.

Figure 8:
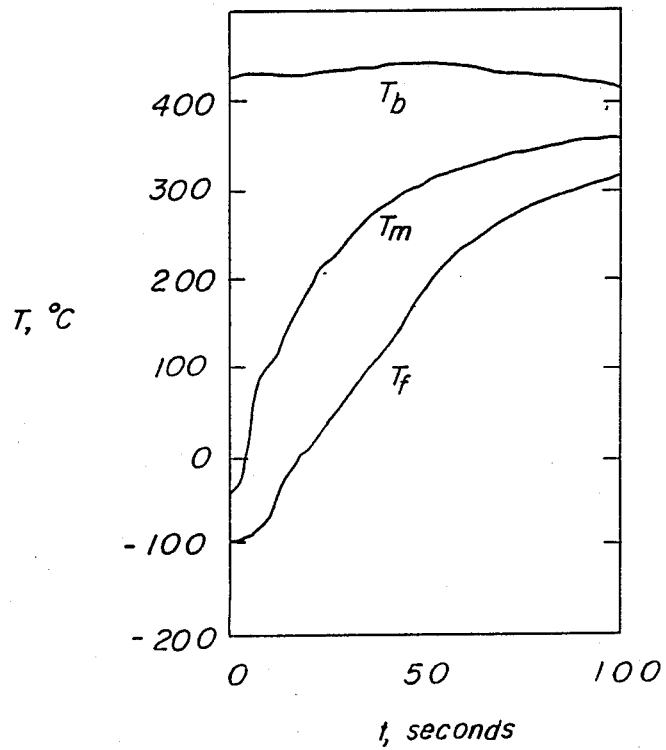
FIG. 8 is a graph showing the temperatures at sample inlet ($T_b$), column midpoint ($T_m$), and sample exit ($T_f$) in one experiment conducted in accordance with the invention and performed with the apparatus shown in FIGS. 5–7; and serves as an example of the contour in FIG. 3.
Figure 9:
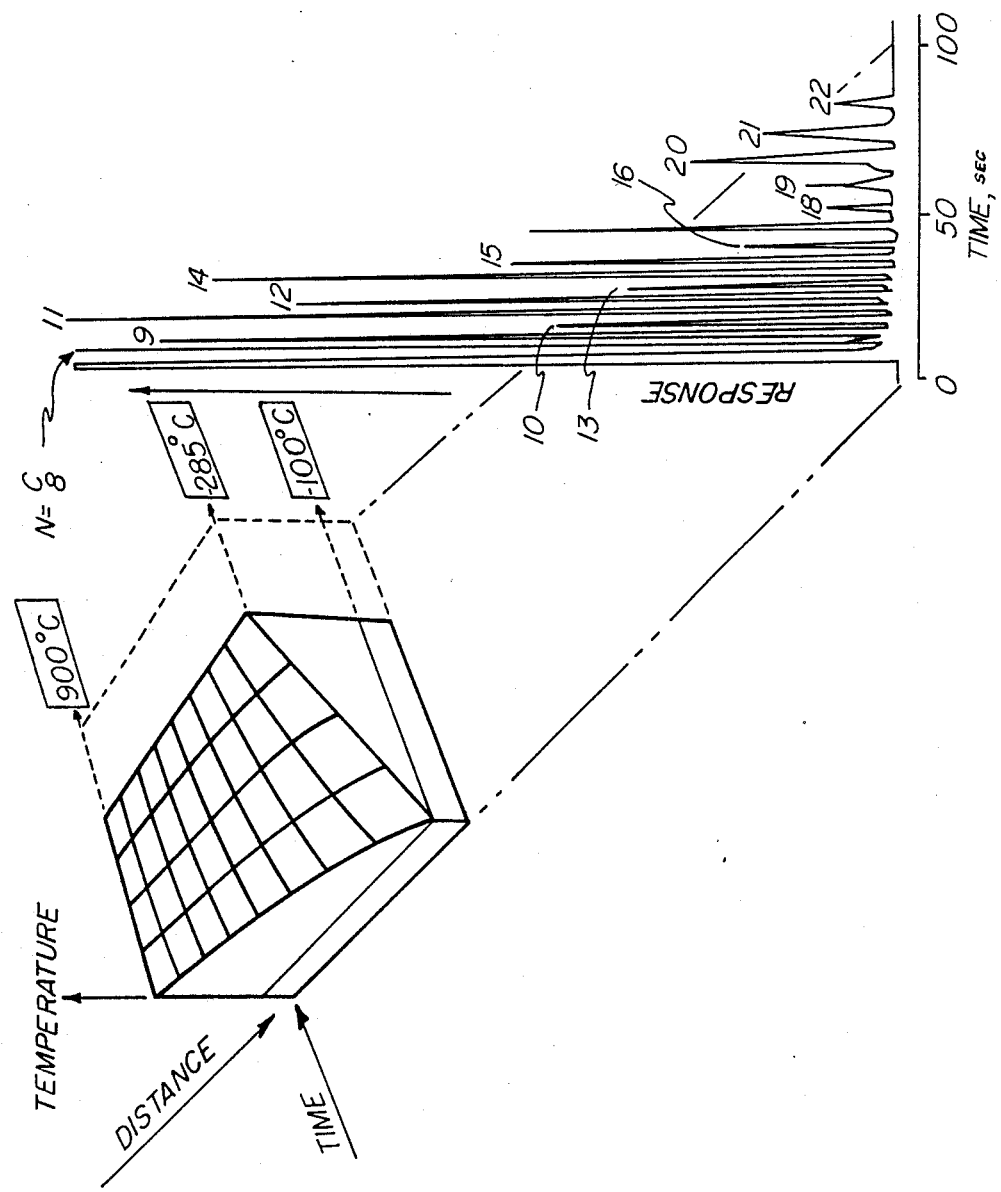
FIG. 9 is a chromatogram of a separation obtained under temperature surface conditions exemplifying the contour shown in FIG. 2.

The operation of the instrument shown in FIGS. 5-7 to produce the time and temperature profile graph of FIG. 8 and the chromatogram of FIG. 9 is as follows.

After the necessary components were assembled as shown in FIG. 5, a 0 to 130 Volt AC Variac was connected to act as the variable voltage source 30 to the input terminals joining the multi-stranded resistance heating wire 12. Also, a room temperature nitrogen gas stream was connected to the bottom plate flowpath at inlet 14 located at the injector end of the column sheath assembly and was caused to exit primarily through port 16. Another nitrogen gas flowpath was connected at 26 to the detector end of the top plate 4 which housed the open tubular column 2 and caused to exit primarily at port 28. The nitrogen supply line (not shown) for this latter nitrogen flowpath contained a large in-line copper coiled tube ($\frac{1}{4}$" O.D.) which was submerged in liquid nitrogen contained in a large insulated Dewar flask. Consequently, variable flows of very cold nitrogen gas (less than minus 100° C.) could be and were admitted counter-currently to the sample flow through column 2 within the top plate 4 through grooves 8.

Once the electrical power source was connected to the heating wire 12 and the two nitrogen gas lines were connected, a flow of purified helium gas was established through the chromatographic column. Thereafter the detector was heated to an elevated temperature (295° C). Then the injector was heated (320° C.) as it had its own separate heating element (not shown) for controlling the temperature of the injector body 20. As the column had previously been conditioned, no additional thermal processing was conducted.

After establishing moderate flows of nitrogen gas in both the bottom plate conduit and the conduit containing the open tubular column, voltage was applied by the Variac 30 and temperature measurements were made at $T_b$, $T_m$, $T_f$. While maintaining a modest flow of nitrogen gas in the bottom plate through the use of a variable pressure regulator 44 with an initial setting of approximately 5 psig, the Variac 30 output voltage was increased until a $T_b$ setting was reached that was in excess of 400° C. The cold nitrogen gas flow admitted through inlet 26 was then increased using adjustable pressure regulator 42 which employed delivery pressures of up to 40 psig to the in-line copper tubing heat exchanger which was connected to the top plate grooves 8. This large flow of nitrogen gas, approximately 10 liters per minute at room temperature and pressure, was capable of producing temperatures at $T_f$ that were lower than minus 100° C. Thus, the temperature near the injector 20, i.e., $T_b$, was in the vicinity of 400° C. while the exit region 22 of the OTC was at approximately minus 100° C. With this particular flow configuration, midpoint temperatures as indicated by $T_m$, were initially at minus 40° C.

Thermal gradient programming with this flow arrangement of nitrogen gas streams was performed by increasing the pressure for the inlet nitrogen gas in the bottom grooves 10 and simultaneously decreasing the gas flow of cold nitrogen gas travelling through grooves 8. Gradually, the flow of cold nitrogen gas would be stopped. These flow changes were made manually using the two respective pressure regulators 44, 42, and the temperature versus time profiles as shown in FIG. 8 were generated. These temperature profiles were produced with an electrical input of 95 volts AC applied to the multi-stranded stranded resistance heating wire 12 by the Variac 30. In this manner, the time and temperature profile graph of FIG. 8 was generated. This particular time and temperature profile is an example of the temperature surface approaching that shown in FIG. 3.

In order to provide the temperature surface and chromatogram shown in FIG. 9, another gas flow arrangement was conducted where now the flow of ambient nitrogen gas was admitted at gas port 16 of the bottom conduit 10 and flowed to exit at port 14. This produced a different distance/temperature/time profile where $T_b$ remained at approximately 300° C., while $T_m$ varied with time from 250° C. to 290° C. and $T_f$ changed from −100° to 285° C. The three-dimensional contoured surface resembled the graphical depiction shown in FIG. 2 (the same as FIG. 9). In this case, a pressure of approximately 20 psig was used for flowing gas through the bottom plate 6, while only 10 psig were needed for cooling the top plate $T_f$ to approximately minus 100° C. In this particular mode, only the cold nitrogen gas experienced a reduction in flow, which eventually stopped.

When a temperature of −100° C. for $T_f$ was reached, a sample was inserted into the injector and after an initial hold period (e.g., 5 seconds) the thermal gradient programming was initiated by reducing the pressure that controlled the cold nitrogen gas flow. This was done manually, and required approximately 20 seconds. The chromatogram resulting from this operation is seen for the n-hydrocarbon solutes ($C_8$-$C_{22}$) shown in FIG. 9.

In order to re-cycle the column sheath assembly for subsequent use and to re-establish the initial thermal contour within the column sheath assembly, it was necessary to merely reapply the 10 psig pressure to the cold nitrogen gas flow path. It was possible to obtain a $T_f$ value of minus 100° C. within approximately 40 seconds after establishing this cold flow of nitrogen gas. This rapid recycling permits subsequent analyses to be performed with minimal delays.

It is interesting to note that these two different thermal gradient programs were produced using a constant applied voltage. Many other electrical power functionalities could be used for generating time-based profiles. Also, it should be noted that at each gas port or terminal shown in FIG. 5, namely ports 14, 16, 26 and 28, there can be five different types of transport behavior. Specifically, there can be flow in the forward direction or the reverse direction. Flow can be restricted and even stopped. In addition, a vacuum line can even be applied at any of the ports.

The conditions and ancillary equipment used in the above-described procedures were as follows:

| | |
|---|---|
| Instrument | Varian 2440 (Modified to have a horizontal HFID, and modified to have an electrometer with a time constant or 50 msec.) |
| Column | tubing material fused silica |
| | tubing length, 2.20 m |
| | tubing inside diameter, 0.20 mm |
| UVD 100 P2 | Stationary phase, Dimethyl Silicone film thickness 0.33 microns |
| Carrier gas, Helium | inlet pressure 1.05 abs atm |
| | initial linear velocity, typ 28 cm sec$^{-1}$ |
| | initial outlet flow, ~1.0 cm$^3$ min$^{-1}$ |
| Detector | type, HFID |
| | range, 10$^{-12}$ A/mv |
| | attenuation, 32 |
| Detector gas flows | hydrogen, 30 cm$^3$ min$^{-1}$ |
| | air, 300 cm$^3$ min$^{-1}$ |
| | column outlet supplement, 25 cm$^3$ min$^{-1}$ |
| Output signal recording | full scale read out, 1.0 mv |
| | chart advance rate, 5.0 cm min$^{-1}$ |
| Sample | description, n-hydrocarbons, ($C_8$-$C_{22}$) |
| | solvent, n-$C_6$ |
| | concentration in solvent, 5% in $C_6$ |
| | injection sample size 0.1 mL |
| | split ratio ~1 to 60 |
| Temperatures | injector: 320° C. |
| | column: as shown in FIG. 9 |
| | detector: 295° C. |

In FIG. 8, $T_b$ represents the temperature at the sample inlet section of the column. $T_m$ is the column mid-point temperature, with $T_f$ being the final exit temperature. The consecutive mixture solutes shown in FIG. 9, n-$C_8$ through n-$C_{22}$, possess a boiling point range of 243° C. and were separated in accordance with the invention in an elapsed time of approximately 80 seconds. $T_f$ here was programmed −100° C. to +285° C. The hydrocarbon mixture could not be easily separated by conventional isothermal gas chromatography and it would require a very much longer time for separation by linear programmed temperature gas chromatography. Furthermore, even if performed by programmed temperature gas chromatography, subsequent analyses would require cooling of a high heat capacity oven, with a concomitant delay of several minutes.

The solute zone disengagements shown in FIG. 9 were as predicted by theory. The ability to program various temperature surfaces, with exit temperatures from very low values (e.g. $T_f = -100°$ C.) to very high values, (e.g. +450° C.) in a time frame of 100 seconds indicates that any gas chromatographable sample could be eluted through an appropriate assembly in accordance with the invention within that same time frame.

Based upon experimental results accumulated so far, the range of operating parameters or conditions for the procedure are:

Carrier gas: $H_2$, He, $N_2$, Ar, $CO_2$
Linear velocity ($v_m$): 5 to 500 cm/sec
Outlet pressure: atmospheric or vacuum
OTC length: 0.5–100 meters
OTC inside diameter: 50 to 1000 microns
Film thickness ($d_f$); 0.01 to 10 microns
OTC cladding: aluminum, polyimide, nickel
Detector: HFID, MS, or any fast responding GC detector
$T_b$: sub-ambient to 500° C.
$T_f$: −180° to +500° C.
$T_h$: 10 to 120 sec
Elapsed analysis time: 20 to 1000 seconds While this invention has been described with respect to particular embodiments thereof, it is apparent that numerous other forms and modifications of this invention will be obvious to those skilled in the art. The appended claims and this invention generally should be construed to cover all such obvious forms and modifications that are within the true spirit and scope of the present invention.

I claim:

1. In a method of performing gas chromatographic analysis wherein a sample is admitted to a chromatographic column and caused to travel in a direction from upstream to downstream from an inlet port of said column to an elution port, the improvement comprising the steps of
    (a) providing temperature control means in thermal transfer relation with said column, said temperature control means being adapted to heat or cool selected locations of said column
    (b) providing a curvilinearly shaped negative temperature gradient along said column by said temperature control means, with the temperature at the elution port of said column being maintained lower than the temperature at the inlet port thereof at all times except for the end of said analysis so that the sample will continuously be subjected to a lower temperature as it travels in a downstream direction along said column, said column and said temperature control means being capable of transferring changes of at least about 0.5° C. per second from said temperature control means to said column and
    (c) raising the temperature of the column at said elution port at the end of said analysis so that said sample will elute from the column.

2. Method as recited in claim 1 wherein said step (a) comprises contacting said column with a flow of cooling fluid.

3. Method as recited in claim 2 wherein the temperature of said cooling fluid is less than about 100° C.

4. Method as recited in claim 3 comprising providing flow of said cooling fluid along and in heat transfer relation with said column from a downstream to upstream portion of said column.

5. Method as recited in claim 2 further comprising regulating the pressure of said cooling fluid.

6. Method as recited in claim 5 further comprising programming variations in said pressure over time.

7. Method as recited in claim 1 wherein said step (a) comprises contacting said column with a flow of ambient temperature fluid.

8. Method as recited in claim 7 wherein said fluid is nitrogen gas.

9. Method as recited in claim 7 comprising providing flow of said ambient temperature fluid along and in heat transfer contact with said column from an upstream to downstream portion of said column.

10. Method as recited in claim 9 further comprising regulating the pressure of said ambient temperature fluid.

11. Method as recited in claim 10 further comprising programming variations in said pressure over time.

12. Method as recited in claim 1 wherein said step (a) comprises providing an electrical resistance heating means in heat exchange relationship with said column.

13. Method as recited in claim 12 further comprising surrounding both said resistance heating means and said column with an insulating sheath assembly.

14. Method as recited in claim 13 further comprising admitting a first heat exchange fluid to said sheath assembly to further regulate the heating or cooling of selected locations of said column.

15. Method as recited in claim 14 wherein said fluid comprises a cryogenic fluid, said method further comprising causing said fluid to flow in said sheath and along said column in a direction from a downstream to upstream portion of said column.

16. Method as recited in claim 15 further comprising varying the pressure of said cryogenic fluid over time.

17. Method as recited in claim 15 further comprising admitting a second heat exchange fluid to said sheath assembly, and causing said second fluid to flow in a direction along said column that is opposite from the flow direction of said first fluid.

18. Method as recited in claim 17 wherein said first fluid is nitrogen having a temperature of about −100° C. or less and wherein said second fluid is nitrogen having an ambient temperature.

19. Method as recited in claim 12 further comprising varying the temperature of said resistance heating means over time.

20. Gas chromatographic apparatus of the type adapted to perform sample separation analysis comprising
    (a) an open tubular chromatographic column having a sample inlet port located at an upstream portion of said column and a sample elution port at a downstream portion of said column,
    (b) temperature control means in thermal transfer relation with said column for imparting a curvilinearly shaped negative temperature gradient along said column whereby the downstream end of said column is maintained at a lower temperature than said upstream portion during all but the endpoint of said analysis, said column (a), and temperature control means (b) being capable of transferring changes of at least about 0.5° C. per second from said temperature control means to said column.

21. Apparatus as recited in claim 20 wherein said temperature control means comprises heater means and a temperature programmer in operative association with said heater means.

22. Apparatus as recited in claim 20 wherein said temperature control means comprises heater means and a temperature and time programmer in operative association with said heater means.

23. Apparatus as recited in claim 20 further comprising an insulating sheath means surrounding said column and wherein said temperature control means comprises a passage formed within said sheath, a source of a first heat transfer fluid being connected with said passage and in heat transfer relation with said column.

24. Apparatus as recited in claim 23 further comprising a programmer means for regulating pressure of said first heat transfer fluid being admitted to said passage.

25. Apparatus as recited in claim 23 further comprising a source of a second heat transfer fluid being connected with said passage and in heat transfer relation with said column.

26. Apparatus as recited in claim 25 further comprising a second programmer means for regulating pressure of said second heat transfer fluid being admitted to said passage.

27. Apparatus as recited in claim 20 further comprising an insulating sheath means surrounding said column with a passage formed in said sheath, said temperature control means comprising heater means disposed in said passage in heat exchange relation with said column.

28. Apparatus as recited in claim 27 further comprising a temperature programmer operatively connected to said heater means for varying the temperature of said heater means over a given period of time.

29. Apparatus as recited in claim 28 wherein said temperature control means also comprises a source of a first heat transfer fluid connected with said passage and means for regulating the pressure of said first heat transfer fluid being admitted to said passage.

30. Apparatus as recited in claim 29 wherein said temperature control means comprising a source of a second heat transfer fluid connected with said passage and means for regulating the pressure of said second heat transfer fluid being admitted to said passage.

31. Gas chromatographic apparatus comprising an open tubular chromatographic column having an upstream sample inlet port and a downstream sample elution port, a heater in thermal transfer relation with respect to said column, fluid regulating means for passing a heat exchange fluid into heat exchange relation with said column, said heater being operatively connected to a time and temperature control programmer and said fluid regulating means being operatively connected to a time and flow rate regulator whereby said heater and fluid regulating means provide a curvilinearly shaped negative temperature gradient along said column with a lower temperature being provided at said elution port than at said inlet port.

* * * * *